(12) United States Patent
Bigus et al.

(10) Patent No.: US 6,629,992 B2
(45) Date of Patent: Oct. 7, 2003

(54) SHEATH FOR SELF-EXPANDING STENT

(75) Inventors: Steve Bigus, San Jose, CA (US);
Orlando M. Padilla, Laguna Niguel, CA (US); Brent Belding, Los Gatos, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/897,743

(22) Filed: Jun. 29, 2001

(65) Prior Publication Data

US 2002/0052640 A1 May 2, 2002

Related U.S. Application Data

(63) Continuation-in-part of application No. 09/632,741, filed on Aug. 4, 2000.

(51) Int. Cl.$^7$ .................................................. A61F 2/06
(52) U.S. Cl. ....................... 623/1.12; 623/1.11; 606/194
(58) Field of Search ....................... 623/1.11, 1.12, 623/1.2, 12, 1.23; 606/108, 191, 192, 194, 195, 198

(56) References Cited

U.S. PATENT DOCUMENTS

| 5,534,007 A | | 7/1996 | St. Germain et al. |
| 5,549,635 A | * | 8/1996 | Solar .......................... 606/198 |
| 5,735,859 A | | 4/1998 | Fischell et al. |
| 5,772,669 A | | 6/1998 | Vrba |
| 5,899,935 A | * | 5/1999 | Ding .......................... 623/1.53 |
| 5,928,258 A | | 7/1999 | Khan et al. |
| 5,957,974 A | * | 9/1999 | Thompson et al. ......... 623/1.13 |
| 6,086,610 A | * | 7/2000 | Duerig et al. .............. 623/1.18 |
| 6,143,016 A | | 11/2000 | Bleam et al. |
| 6,290,722 B1 | * | 9/2001 | Wang ......................... 623/1.46 |
| 6,379,379 B1 | * | 4/2002 | Wang ......................... 623/1.15 |
| 2001/0053929 A1 | * | 12/2001 | Vonesh et al. ............. 623/1.12 |
| 2002/0138129 A1 | * | 9/2002 | Armstrong et al. ........ 623/1.11 |

* cited by examiner

Primary Examiner—David J. Isabella
Assistant Examiner—Urmi Chattopadhyay
(74) Attorney, Agent, or Firm—Fulwider Patton Lee & Utecht, LLP

(57) ABSTRACT

A catheter assembly for delivering an endoprosthesis within a body lumen. A delivery catheter assembly is provided which includes a stent with biocompatible material thereon for preventing the stent from expanding or otherwise dislodging from the catheter. The stent with biocompatible material is secured to an expandable member of a delivery catheter, whereby inflation of the expandable member causes the biocompatible material to fail, thereby permitting the stent to expand and deploy in a body lumen.

5 Claims, 10 Drawing Sheets

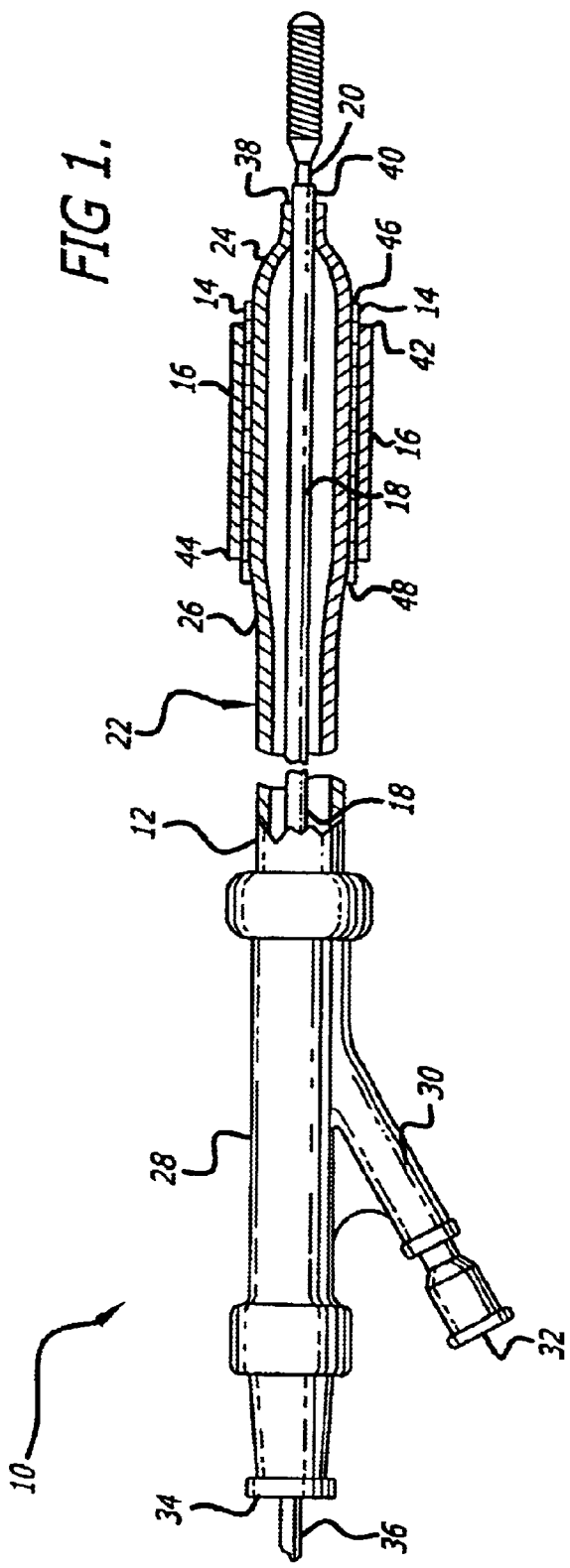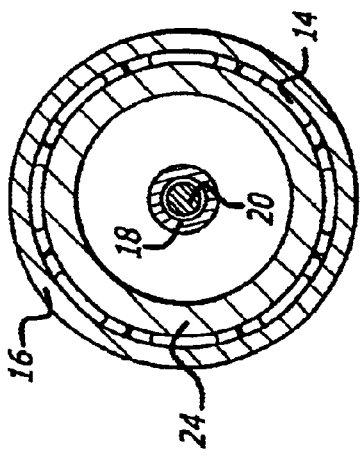

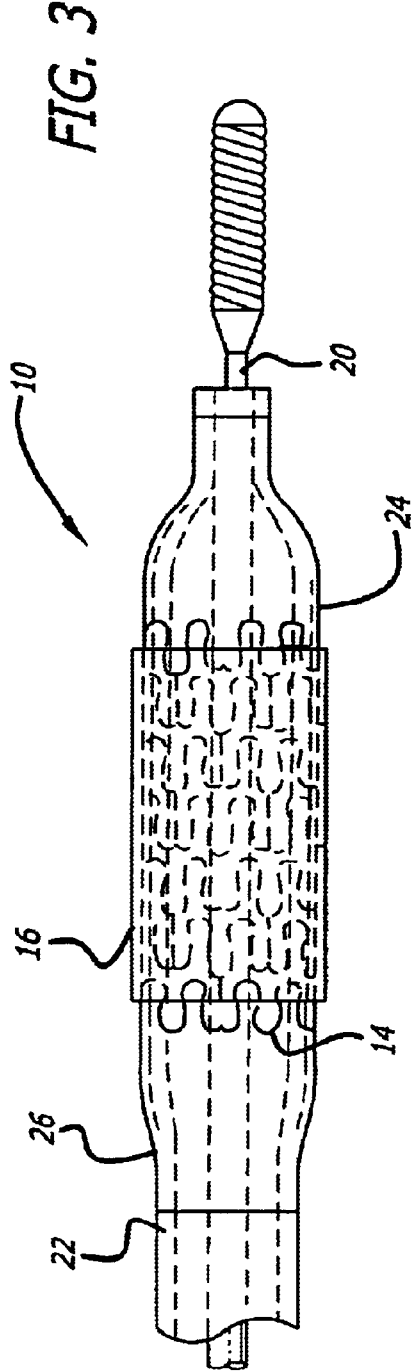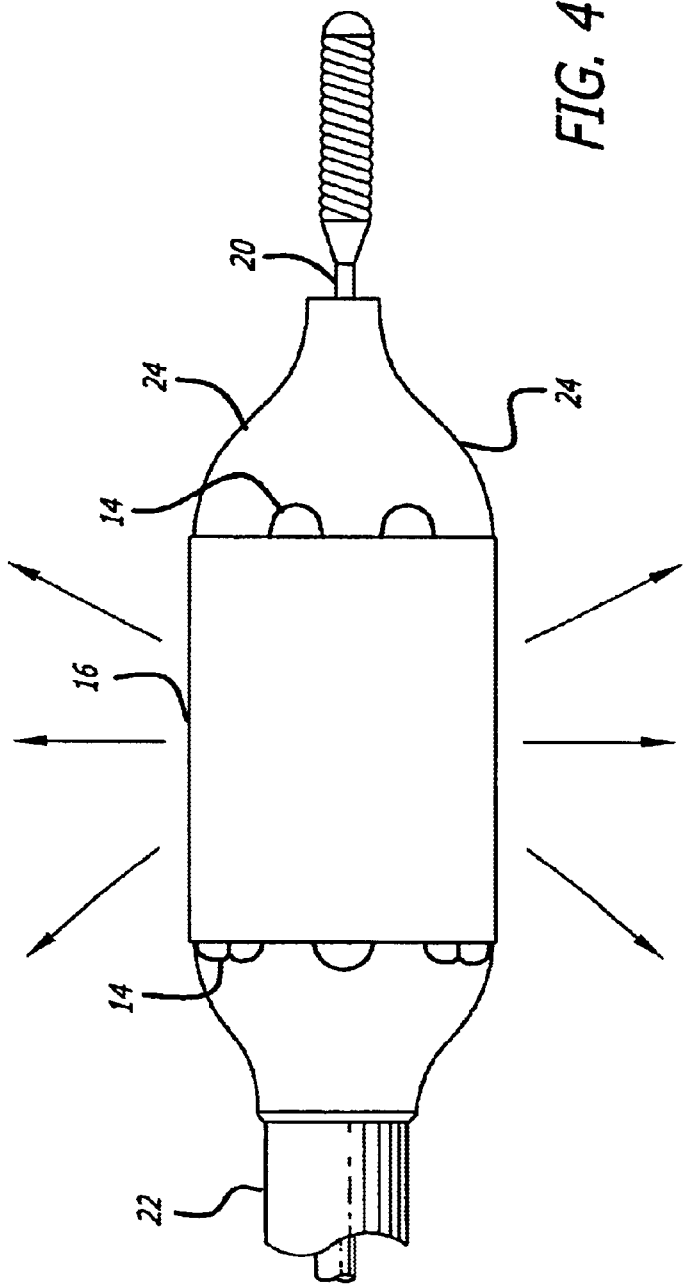

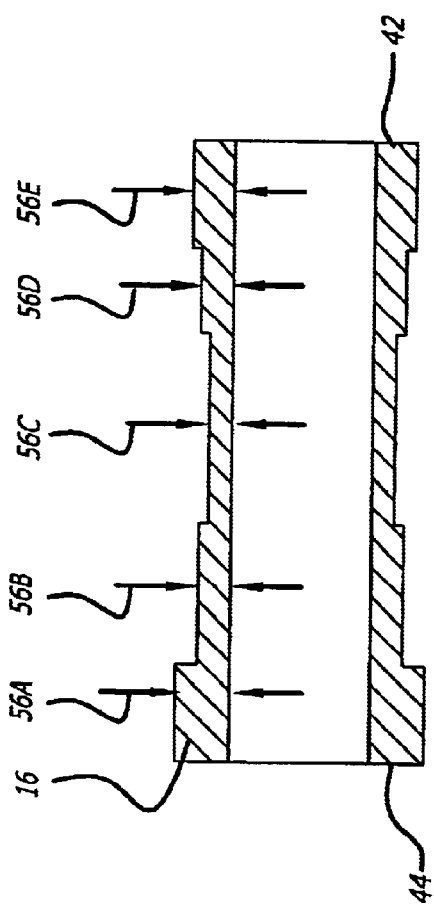
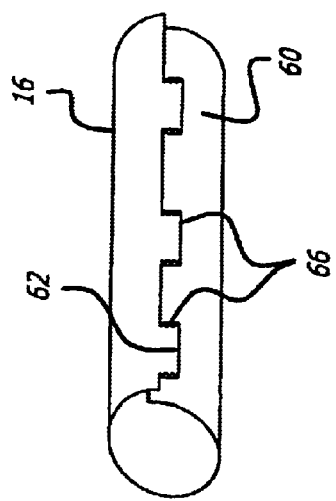
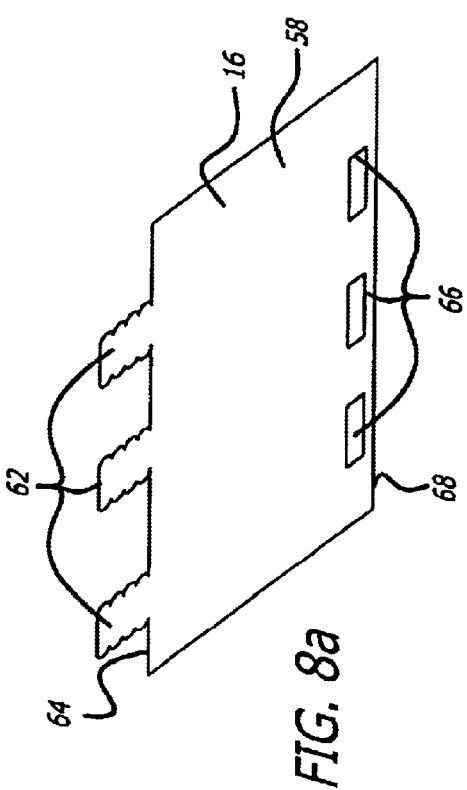

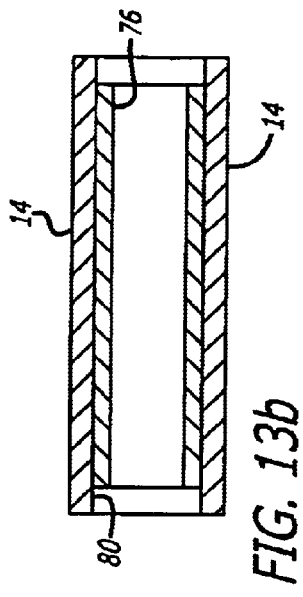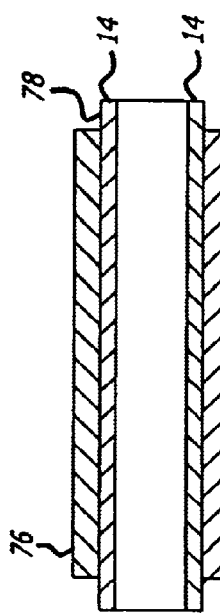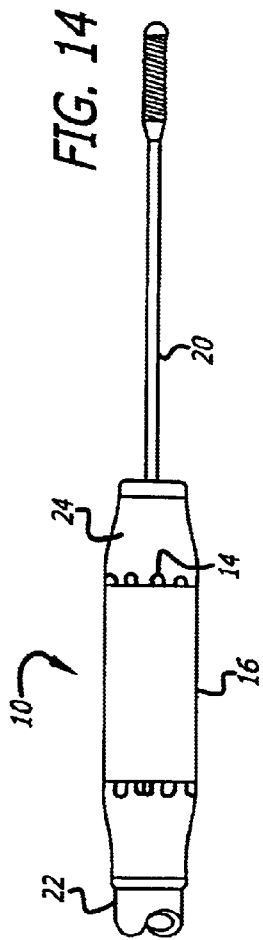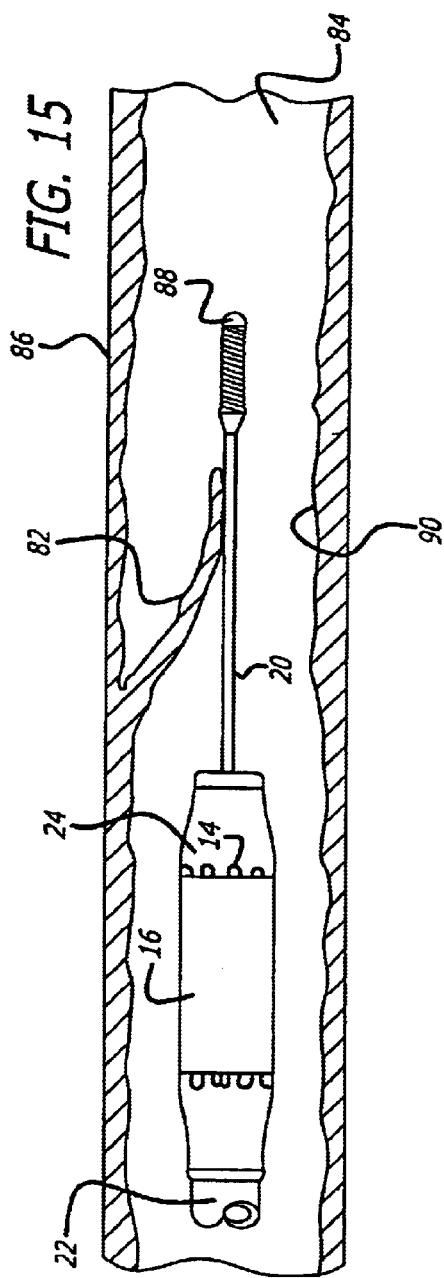

SHEATH FOR SELF-EXPANDING STENT

CROSS-REFERENCE TO RELATED APPLICATIONS

The present application is a continuation in part of U.S. Ser. No. 09/632,741, filed Aug. 4, 2000, and entitled DETACHABLE SHEATH TO PROVIDE PRE-DEPLOYMENT STENT SECURITY AND ENHANCED DELIVERY PRECISION.

BACKGROUND OF THE INVENTION

This invention relates to apparatus and methods for the treatment of body lumens, and particularly to delivery systems for endoprostheses. More particularly, the invention relates to biocompatible and/or bioabsorbable sheaths for self-expanding stents. The present invention also is directed to a delivery system for self-expanding stents which facilitates minimal stent movement during deployment to achieve more accurate stent placement within the patient's vasculature.

Several interventional treatment modalities are presently used for heart disease including balloon and laser angioplasty, atherectomy and by-pass surgery. In a typical cardiovascular intervention, a guiding catheter having a preformed distal tip is percutaneously introduced over a first wire, such as a 0.035" wire, that has been placed in the vasculature through a guiding sheath into an artery and advanced within the cardiovascular system until the distal tip of the guiding catheter is seated in the ostium of a coronary artery. The first wire is removed and a guidewire, such as a 0.014" guidewire, is advanced distal to the treatment area. Then a dilatation catheter is back-loaded onto the guidewire and tracked to the treatment area through the guiding catheter. Once in position across the lesion, the balloon is inflated to a predetermined size with radiopaque liquid at relatively high pressure (e.g., greater than four atmospheres) to compress the plaque of the lesion and to otherwise expand the inner lumen of the artery.

Further details of dilatation catheters, guidewires, and devices associated therewith for angioplasty procedures have been known for a number of years, and by way of example, several forms of such devices can be found in U.S. Pat. No. 4,323,071 (Simpson-Robert); U.S. Pat. No. 4,439,185 (Lindquist); U.S. Pat. No. 4,516,972 (Samson); U.S. Pat. No. 4,538,622 (Samson, et al.); U.S. Pat. No. 4,554,929 (Samson, et al.); U.S. Pat. No. 4,616,652 (Simpson); U.S. Pat. No. 4,638,805 (Powell); U.S. Pat. No. 4,748,982 (Horzewski, et al.); U.S. Pat. No. 5,507,768 (Lau, et al.); U.S. Pat. No. 5,514,154 (Lau, et al.); U.S. Pat. No. 5,451,233 (Yock); and U.S. Pat. No. 5,458,615 (Klemm, et al.); and U.S. Pat. No. 5,700,286 (Tartaglia, et al.).

A focus of recent development work in the treatment of heart disease has been directed to endoprosthetic devices called stents. Stents are generally cylindrically shaped intravascular devices which are placed within an artery to hold it open. The device can be used to reduce the likelihood of restenosis and to maintain the patency of a blood vessel immediately after intravascular treatments. In some circumstances, they can also be used as the primary treatment device where they are expanded to dilate a stenosis and then left in place.

Prior art stents typically fall into two general categories of construction. The first type of stent is expandable upon application of a controlled force, often through the inflation of the balloon portion of a dilatation catheter which, upon inflation of the balloon or other expansion means, expands the compressed stent to a larger diameter to be left in place within the artery at the target site. The second type of stent is a self-expanding stent, which may be formed from shape-memory metals such as super-elastic nickel titanium (NiTi) alloys which will automatically expand from a compressed state when the stent is advanced out of the distal end of the delivery catheter into the body lumen. Such self-expanding stents can typically be expanded without the need for application of a controlled force on the stent, such as is applied through the inflation of the balloon portion of a dilatation catheter. Such self-expanding stents may be manufactured from expandable heat-sensitive materials that allow for phase transformation of the materials to occur at set temperatures, resulting in the expansion and/or contraction of the stents.

One method and system developed for delivering stents to desired locations within the patient's body lumen involves advancing the stent delivery system through the patient's vascular system until the stent is positioned within the treatment area, and then inflating the expandable member on the catheter to expand the stent within the blood vessel. The expandable member is then deflated and the catheter withdrawn, leaving the expanded stent within the blood vessel, holding open the passageway thereof. This approach is common with stents of the first type, i.e., stents that are not self-expanding.

Implanting self-expanding stents within the patient's vasculature often require different methods than the one set forth above for non-self-expanding stents. Some prior art stent delivery systems for self-expanding stents include a catheter with an inner lumen upon which the compressed or collapsed stent is mounted, and an outer restraining sheath which is eventually placed over the compressed stent prior to deployment. When the stent is to be deployed in the body vessel, the outer sheath is moved in relation to the inner lumen to "uncover" the compressed stent, allowing the stent to move to its expanded condition. Some delivery systems utilize a "push-pull" technique in which the outer sheath is retractable while the inner sheath is pushed forward or held in place. Still other systems use an actuating wire which is attached to the outer sheath. When the actuating wire is pulled to retract the outer sheath over the collapsed stent, the inner lumen must remain stationary, preventing the stent from moving axially within the body vessel.

Because proper positioning of the stent is critical to the performance of the stent, it is imperative that the physician knows exactly where the stent will be placed upon deployment.

What has been needed and heretofore unavailable is an improved device and method for accurately providing for release and deployment of stents, including self-expanding stents. The present invention satisfies these and other needs.

SUMMARY OF THE INVENTION

Briefly, and in general terms, the present invention is directed to a bio-compatible or bio-absorbable addition to a stent and/or stent delivery system. More particularly, the invention relates to a bio-compatible or bio-absorbable sheath, lining, or filament positioned on or in a stent. The bio-compatible or bio-absorbable material is designed to be implanted in the body along with the stent. After implantation, the material may be absorbed into the body, such as where the material is a bio-absorbable material that dissolves over a period of time.

In one embodiment of the invention, a bio-absorbable or bio-compatible filament is wound through or around an expandable stent. The filament may have sufficient strength to help in constraining the stent in an unexpanded configuration. Such a filament may still have sufficient weakness to permit the stent to be expanded via the application of a force, such as via the application of force provided by the expansion of a balloon catheter where the stent is positioned on the balloon. Expansion of the stent may be achieved by applying sufficient force to cause the filament to break or otherwise fail or relax. Expansion of the stent may be achieved by changing the configuration of the filament, such as by pulling or pushing, proximally or distally, on the filament until it no longer provides sufficient restraint to prevent the stent from expanding. The filament may be formed from various materials, including polymers. The filament may comprise one or more therapeutic agents, such as a drug useful in treating arterial walls.

Such a filament may be bonded to the delivery catheter and/or the stent, such as where a polymer filament is heat-bonded in a tightly-coiled position around the stent. During stent deployment, which may be achieved through inflation of a balloon catheter, the bonding of the filament to the stent and/or delivery catheter may fail, in whole or in part, loosening the tightness of the filament around the stent and permitting the stent to expand.

The filament maybe used to constrain self-expanding stents to prevent their expanding prior to the desired time and position for stent deployment. The filament may also be used with non-self-expanding stents, such as balloon-expandable stents, to help to retain the stent on a delivery system, such as a delivery catheter. The filament may also comprise and/or be used to deliver therapeutic agents, such as drugs or radiation therapy materials, or other materials that improve stent delivery, deployment, and/or performance, including materials that improve stent visibility under fluoroscopy or that facilitate radiation therapy.

In a further embodiment of the invention, the bio-compatible and/or bio-absorbable material forms a sheath and/or coating that surrounds the stent, in whole or in part. Like the filament, the sheath and/or coating may have sufficient strength to help in constraining the stent in an unexpanded configuration, and may still have sufficient weakness to permit the stent to be expanded by applying sufficient force to cause the sheath to break or otherwise fail and/or relax. The sheath and/or coating may be formed from various materials, including polymers, and may comprise one or more therapeutic agents. In the case of a coating that is bonded to the stent, the coating may be applied to the inner or outer surface of the stent.

In a further embodiment of the invention, the bio-compatible and/or bio-absorbable material is positioned in openings in the stent itself. For example, the material may be positioned to fill one or more of the openings in an expandable stent pattern. In stents that require such openings to change shape during stent expansion, the material may serve to prevent stent expansion by preventing the openings from changing shape. For example, the material may serve as an adhesive that holds the sides of the opening in close proximity to one another, thereby preventing the stent from expanding. The material maybe configured to fail or otherwise relax when sufficient force is applied to expand the stent, such as the force applied by inflation of a catheter balloon.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 1 depicts, in cross-section, a partial side view of an embodiment of a catheter assembly, including stent and bio-compatible sheath of the present invention.

FIG. 2 depicts, in cross-section, an end view of the embodiment of FIG. 1 of a catheter assembly of the present invention.

FIG. 3 depicts a partial side view of the embodiment of FIG. 1 of a catheter assembly of the present invention.

FIG. 4 depicts a partial side view of the catheter assembly of FIG. 3, wherein the balloon is expanded, thereby causing the bio-compatible sheath to fail and permit the stent to expand.

FIG. 7 depicts, in cross-section, a side view of a biocompatible sheath according to an embodiment of the invention.

FIGS. 8a–b depict perspective views of a biocompatible sheath according to an embodiment of the invention.

FIG. 13a depicts a perspective view of stent having a coating of bio-compatible material in accordance with an embodiment of the invention.

FIG. 13b depicts a perspective view of stent having a coating of bio-compatible material in accordance with an embodiment of the invention.

FIG. 14 depicts a partial side view of a stent delivery catheter assembly, including a stent and bio-compatible sheath of the present invention.

FIG. 15 depicts a partial side view of the stent delivery catheter assembly of FIG. 14, including a stent and bio-compatible material of the present invention, partially inserted within a patient's vessel (shown in cross-section).

DESCRIPTION OF THE PREFERRED EMBODIMENTS

Figure 5:
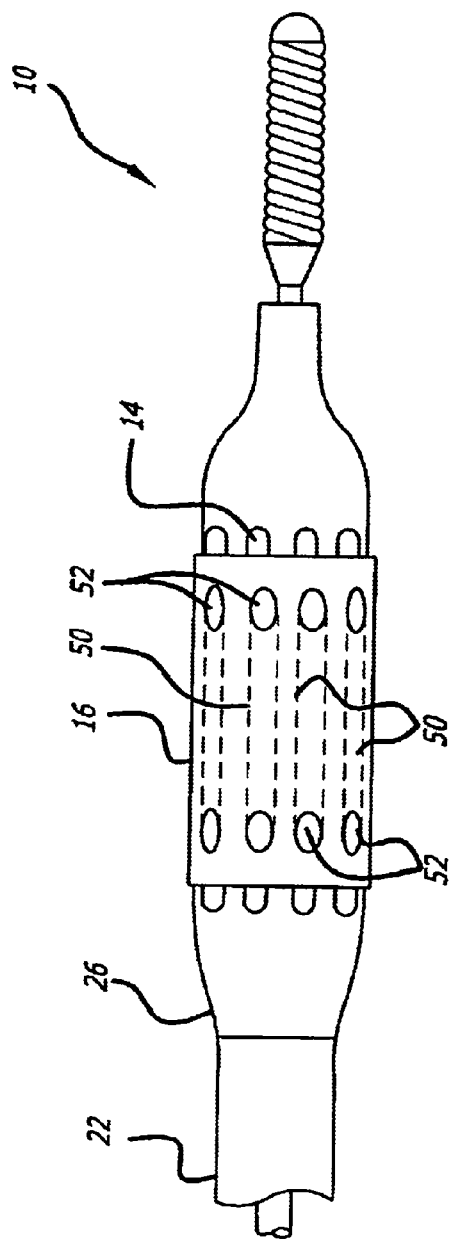
FIG. 5 depicts a perspective view of a biocompatible sheath according to an embodiment of the invention.

The present invention is depicted in FIGS. 1–18 for use in various body lumens and procedures, including use in dilated arteries during balloon angioplasties. The stent may be used to ensure the patency of the body lumen in which it is implanted. For example, the stent may be implanted in the coronary to reinforce the artery against recoil or to tack up a dissection in the arterial wall. The stent is useful for implanting in other blood vessels, such as the carotid arteries, illiacs, cerebral vasculature, and other peripheral veins and arteries. However, the present invention is not limited to use in blood vessels or angioplasties, but can be used in other body lumens and procedures, including treatment of urinary, digestive, or bile ducts.

FIG. 1 depicts a catheter assembly 10, including a delivery catheter 12, an endoprosthesis (depicted as a stent 14), and a bio-compatible sheath 16. The catheter assembly of the particular embodiment depicted includes an inner elongate tubular member 18 configured to encompass a guidewire 20 positioned to slide within an inner lumen of the inner elongate tubular member 18. An outer catheter tube 22 is disposed on and secured to the inner elongate tubular member 18. The catheter assembly 10 includes an expandable member, which in the embodiment depicted is a balloon 24, formed on or secured to catheter tube 22 at the distal portion 26 of the catheter assembly 10 The catheter tube further has a proximal portion 28, which may include a sidearm 30 with an inflation port 32 in fluid communication with the catheter tube 22, and may include a guidewire port 34 in communication with a proximal end 36 of the inner elongate tubular member 18. In addition, the catheter tube 22 has a distal end 38 which is glued, bonded, heat shrunk, or otherwise secured to the inner elongate tubular member 18 near its distal end 38.

The expandable balloon 24 is formed just proximal of the distal end 38 of the catheter tube 22. In the embodiment of FIG. 1, the expandable balloon 24 forms a part of the catheter tube 22. Alternatively, the balloon 24 can be a separate element of the catheter assembly 10, which may be secured to and in fluid communication with a lumen in the proximal portion of the catheter tube 22. In such a configuration, the inner elongate tubular member 18 may not be a necessary element of the catheter assembly, and the guidewire may be disposed within a separate lumen of the catheter tube.

With the stent 14 positioned on the expandable balloon 24, the stent 14 is crimped or otherwise disposed on the catheter tube 22. As shown in FIG. 2, the non-solid, lattice nature of many of the present day stent configurations may result in a non-uniform application of the stent elements on the balloon. Furthermore, to reduce the overall profile of the catheter assembly, the expandable balloon may be folded such that the cross-section of the folded expandable balloon is not circular in nature. In many stent delivery catheters, the expandable member is a dilatation balloon having been arranged in a multiple-fold or no-fold configuration prior to positioning the stent on the balloon.

The catheter assembly 10 includes a biocompatible sheath 16, which is disposed over the endoprosthesis (stent) 14. In the embodiment of FIG. 1, the sheath 16 is longitudinally shorter than the stent 14. The sheath 16 is positioned with its distal end 42 and its proximal end 44 lying between the distal end 46 and proximal end 48 of the stent 14. The sheath 16 also overlies the catheter balloon 24, with the stent 14 positioned there between. The biocompatible sheath 16 at least partially surrounds the stent 14, preventing the stent 14 from expanding, becoming dislodged from the catheter, or contacting the patient's vasculature during stent delivery. The biocompatible sheath 16 may resist outward pressure from the stent 14, particularly where the stent is a self-expanding stent, to prevent the stent 14 from expanding or otherwise dislodging from the balloon 24. Depending on the particular application, the biocompatible sheath 16 may exert continuous inward pressure on the stent 14.

The length of the biocompatible sheath 16 can vary depending on the particular application and catheter assembly construction. For example, a longer biocompatible sheath may be used with longer stents, and a shorter sheath can be used with shorter stents. The biocompatible sheath maybe the same length of the stent, so that the proximal and distal ends of the sheath can align with proximal and distal ends of the stent, respectively, thereby covering the entire length of the stent when mounted on the catheter assembly. The sheath may be longer than the stent, so that it overlaps the distal and/or proximal ends of the stent when mounted on the catheter assembly.

The biocompatible sheath maybe formed from various materials, including various formulations of polyurethane, silicon, siliconized polyurethane, PTFE, and siliconized PTFE. The biocompatible sheath may be formed partially or entirely of bioabsorbable materials, such as sucrose or polyethylene glycol. The biocompatible material may also comprise and/or be used to deliver therapeutic agents, such as drugs or radiation therapy materials, or other materials that improve stent delivery, deployment, and/or performance, including materials that improve stent visibility under fluoroscopy or that facilitate radiation therapy.

Referring to FIGS. 3–4, the biocompatible sheath 16 is configured to fail, such as by stretching or tearing, upon expansion of the expandable balloon 24 of the catheter tube 22. Depending on the application, it may be preferable for the biocompatible sheath 16 to fail at a pressure lower than that of a nominal inflation pressure of the balloon 24, where the nominal inflation pressure is the pressure at which the balloon would, without restraint such as that provided by a biocompatible sheath, reach a specified diameter. For example, with a balloon having a nominal inflation pressure of 8 atmospheres, the sheath may be configured to fail at an inflation pressure of two atmospheres. Accordingly, the sheath 16 will fail well before the balloon 24 reaches its nominal pressure.

As shown in FIG. 4, introduction of inflation fluid (air, saline, etc.) into the catheter tube 22 causes the expandable member 24 to expand radially outwardly. The expansion of the expandable member 24 expands the stent 14, causing the biocompatible sheath 16 to fail. In the embodiment of FIG. 4, the biocompatible sheath 16 fails by plastically deforming. Once the balloon 24 is fully expanded, the stent 14 also becomes fully expanded, with the biocompatible sheath 16 remaining on the stent 14.

In the embodiment depicted in FIGS. 3–4, the sheath 16 has a generally solid, consistent surface and cross-section. In additional embodiments, the sheath may have areas that are weaker than other portions, so that the sheath will fail at the weaker portions. The weakened portions can be created by softening the desired area of the sheath with heat, or otherwise deforming the structure of the sheath material at the desired location. For example, the sheath 16 may have scoring 50 and/or one or more perforations 52, as depicted in FIG. 5, so that the sheath will fail at the scored and/or perforated sections when it is expanded.

Figure 6:
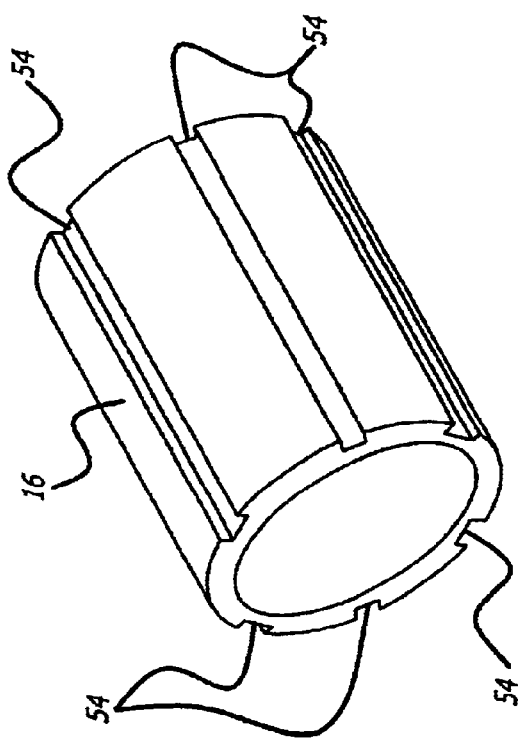
FIG. 6 depicts, in partial cross-section, a perspective view of a biocompatible sheath according to an embodiment of the invention.

The sheath may have thinned portions 54 that have thinner material than other portions of the sheath 16, as depicted in FIG. 6, so that the sheath 16 when expanded will fail at the thinner portions 54.

The weakened areas (e.g., scoring 50, perforations 52, and/or thinner portions 54) may be selectively positioned about the sheath so that the sheath fails in a selected and controlled manner. Depending on the particular application and sheath configuration, the positioning of the weakened portions can assist in controlling stent deployment. For example, the biocompatible sheath 16 may have areas of varying strength across its length, so that certain portions of the sheath will fail sooner than others. In the embodiment depicted in FIG. 7, the biocompatible sheath 16 has varying strength along its length, which in the particular embodiment are achieved by having varying thicknesses 56a–e along its length. The areas with the greatest thickness 56a, 56e are at the distal and proximal ends 42, 44 of the sheath 16, respectively. The sheath 16 is progressively thinner toward its center, with the area with the least thickness 56c along the longitudinal center of the sheath 16. The thickened and stronger proximal and distal portions of the sheath will resist stent expansion (and hence resist balloon expansion) with the greatest force. Such selective positioning of thicker portions can help to control uneven balloon and stent expansion, such as "dog-boning" where the distal and proximal portions of the balloon and stent are expanded prior to the central portions of the balloon and stent.

In a further embodiment depicted in FIGS. 8a–b, the sheath 16 may be formed by rolling a planar portion 58 into a tubular member 60. In the embodiment depicted, the planar portion 58 is held in the tubular shape by mechanical connections, which are scored and/or shaped arm elements 62 on a first end 64 of the planar portion 58 that interlock with openings 66 on an opposing second end 68 of the planar portion. Depending on the particular application, the opposing ends 64, 68 of the planar portion 58 may be held by other methods and devices, including other mechanical connections, heat bonding, and/or adhesives.

Figure 9:
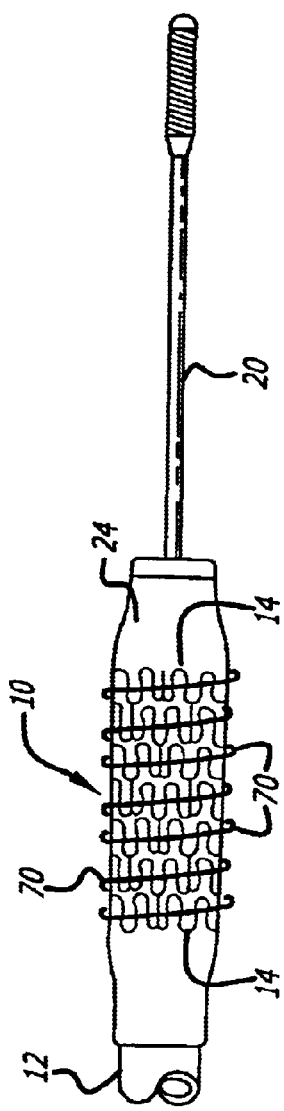
FIG. 9 depicts a partial side view of an embodiment of a catheter assembly, including stent and bio-compatible filament of the present invention.

FIG. 9 depicts another embodiment of the invention, with a catheter assembly 10 that includes a delivery catheter 12, an endoprosthesis (depicted as a stent 14), and a biocompatible filament 70. The biocompatible filament 70 is wrapped around the stent, preventing the stent 14 from expanding or becoming dislodged from the catheter during stent delivery. The biocompatible sheath 16 may exert continuous inward pressure on the stent 14, particularly where the stent is a self-expanding stent. The filament may be wrapped around the stent and, depending on the particular application and stent configuration, the filament may be woven through openings in the stent structure.

The filament may be configured to fail or otherwise loosen its grip on the stent through various methods. For example, the filament 70 may be configured to fail as pressure is applied, as where the balloon 24 is expanded to force the stent 14 to expand against the restraint of the filament 70. As with the sheaths 16 described previously with respect to FIGS. 1–8, the filament 70 of FIG. 9 may have areas that have been weakened, such as perforations, thinned areas, or other methods of weakening the filament structure. The filament 70 maybe threaded or knotted about and/or through the stent so that, when sufficient pressure is applied (such as the pressure from an expanding balloon 24), the knotting and/or threading permits the filament to loosen its inward pressure on the stent, so that the stent is expanded as the filament loosens. The filament may also be secured, such as through heat bonding, to the stent, the balloon, the catheter, and/or to the filament itself, so that the securing device and/or method (e.g., the heat bond) will fail as the balloon is pressurized, thereby expanding the stent. For example, a polymeric filament may wrapped around a stent on a catheter, and then the filament may be heat bonded to the stent. The wrapping of the filament, in combination with the heat bond, can firmly hold the stent onto the balloon during stent delivery. When the balloon is pressurized during stent deployment, the heat bonding will fail, causing the filament to loosen its hold on the stent and permitting the stent to expand.

Figure 10:
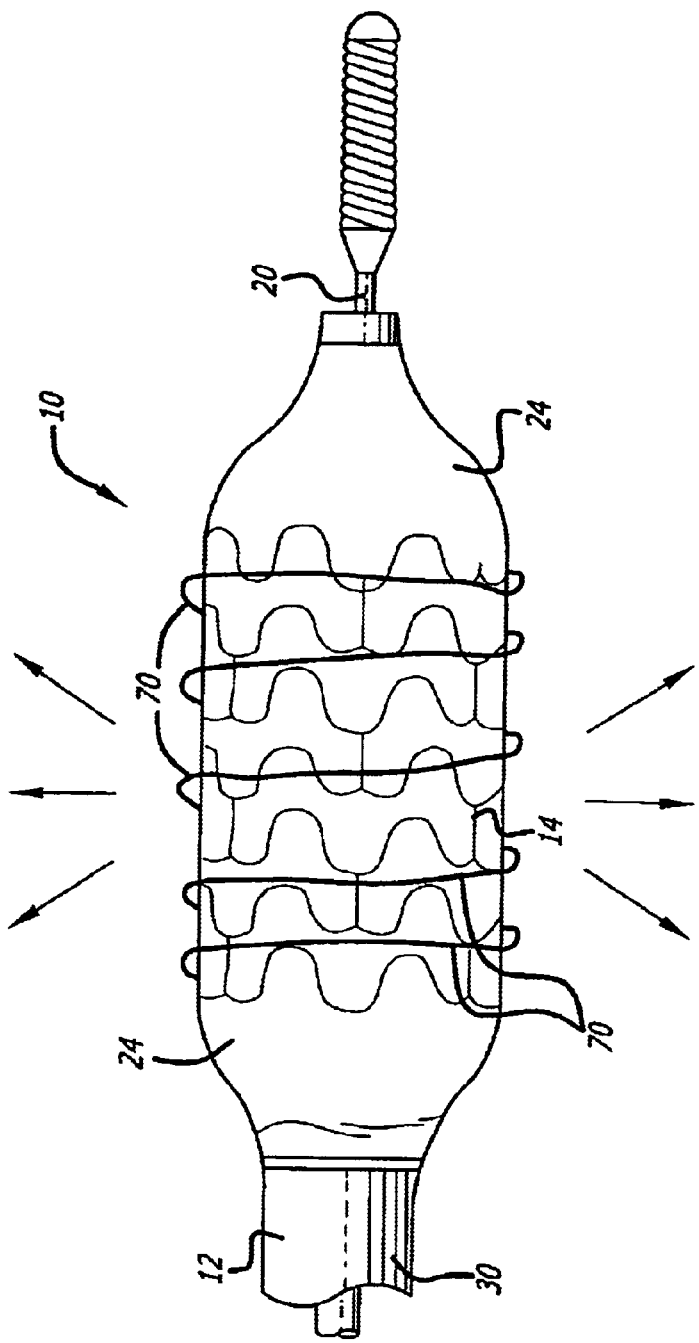
FIG. 10 depicts a partial side view of the catheter assembly of FIG. 8, wherein the filament is relaxed and the stent is expanded.

The filament 70 may be configured to fail through methods other than the application of expansion pressure such as that provided by the balloon and/or stent. For example, the filament may be configured to loosen when a portion of the filament is pulled. FIG. 10 shows the catheter assembly 10 of FIG. 9, wherein the filament 70 has failed or otherwise loosened its hold, and the stent 14 is expanded.

Figure 11:
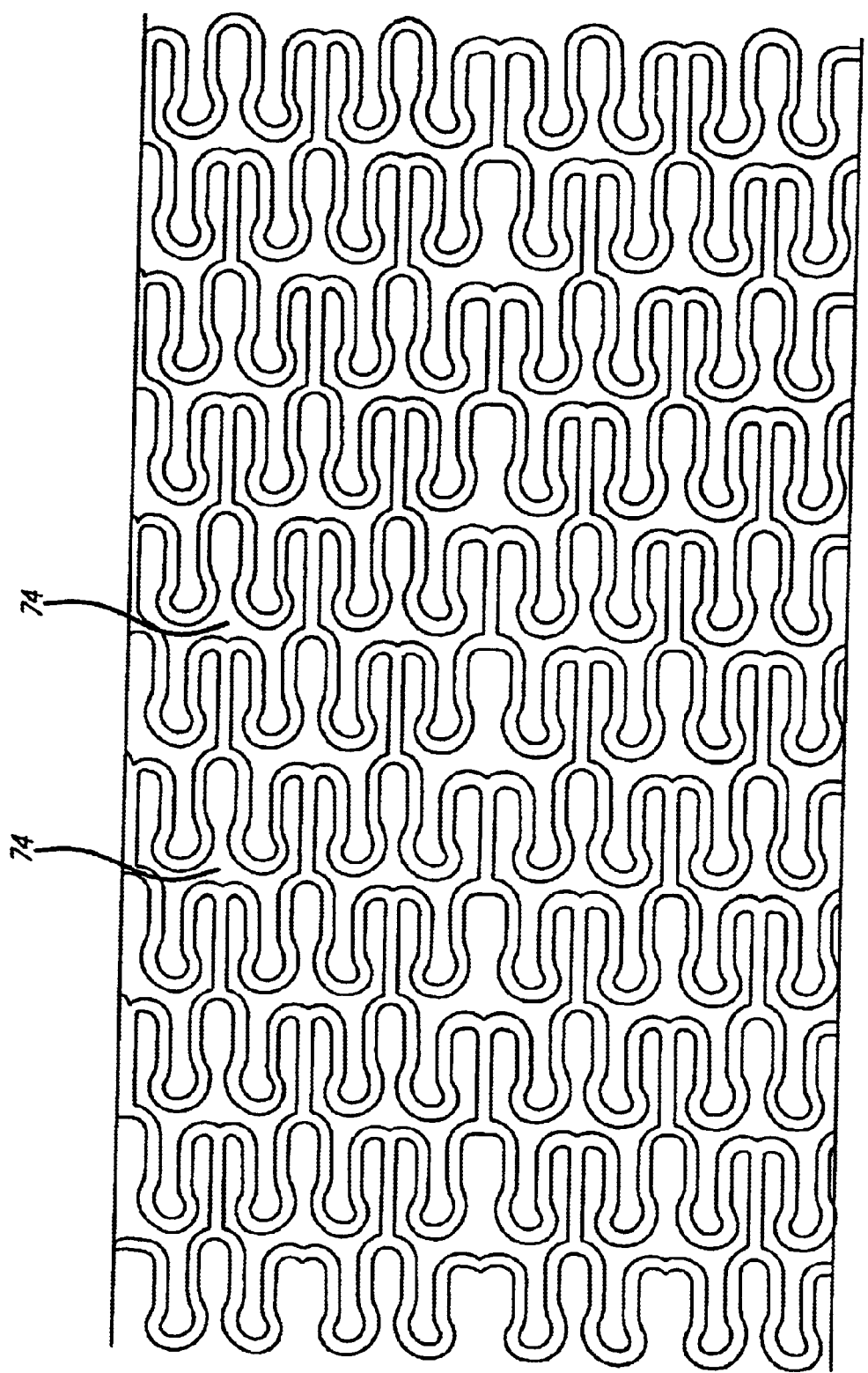
FIG. 11 depicts a view of a stent pattern, with bio-compatible material filling spaces within the stent pattern, in accordance with the stent in the unexpanded condition.
Figure 12B:
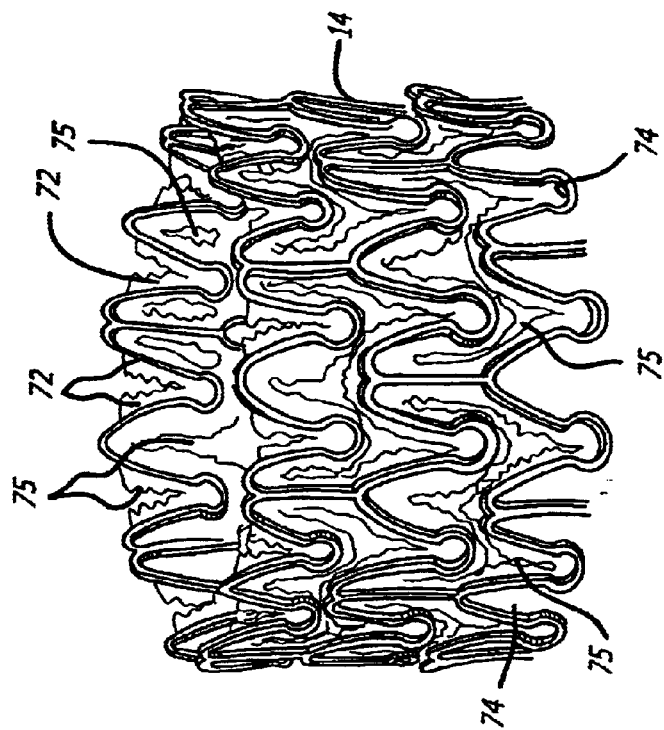
FIG. 12b depicts a perspective view of the stent portion of FIG. 12a, with bio-compatible material within its spaces, wherein the stent is in an expanded condition.
Figure 12A:
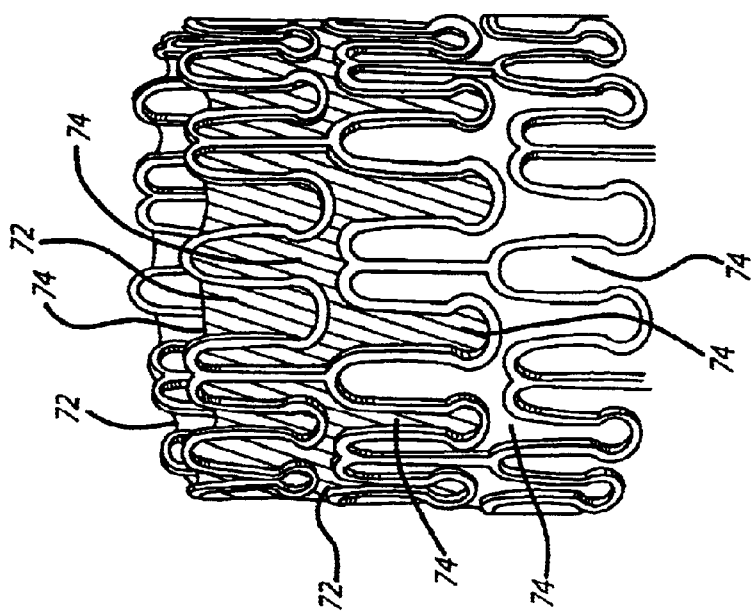
FIG. 12a depicts a perspective view of a stent portion with bio-compatible material within its spaces in accordance with an embodiment of the invention.

Referring now to FIGS. 11–12, a further embodiment of the invention involves a stent 14 with an open-lattice configuration, with bio-compatible material 72 filling one or more of the open areas 74 within the stent pattern. FIG. 11 depicts the stent pattern two-dimensionally as if the tubular stent 14 were cut longitudinally and "unrolled" to form a flat sheet, while FIGS. 12a–b depict a portion of the stent 14 in a perspective view. The pattern depicted includes a series of stent structures (depicted in the form of Us, Ws, and Ys), with vacated or open areas 74 between the stent structures. FIGS. 11 and 12a depict the open-lattice stent 14 in the unexpanded condition, with open areas 74 in which biocompatible material 72 has been loaded.

As depicted in FIG. 12b, when an open-lattice stent 14 such as the one depicted is expanded, the open areas 74 deform in shape. The biocompatible material 72 loaded in the open areas 74 resists such deformation of the open areas 74, thereby preventing the stent 14 from expanding. For example, the bio-compatible material 72 may serve as an adhesive that holds together the stent structure surrounding the open areas 74, thereby preventing the stent 14 from expanding. The biocompatible material 72 maybe configured to fail or otherwise relax when sufficient force is applied to expand the stent 14, such as the force applied by inflation of a catheter balloon upon which the stent is mounted. FIG. 12b shows fractures 75 in the biocompatible material 72 in the open spaces 74, created when the biocompatible material 72 in the open spaces 74 failed as pressure was applied to expand the stent 14.

FIG. 13a shows a further embodiment of the invention, with the stent 14 having a coating 76 of bio-compatible material on the stent outer surface 78. The coating 76 forms a shell on the outer surface of the stent 14, which acts to prevent the stent 14 from expanding, becoming dislodged, and/or contacting the contacting the patient's vasculature during stent delivery. The coating 76 maybe adhered to the outer surface of the stent 14. Depending on the particular application, portions of the coating 76 may extend into open areas of the stent 14, such as with a stent having an open-lattice configuration. As discussed above with respect to FIGS. 11–12, the biocompatible material that extends into the open areas of the stent 14 may provide further opposition to expansion of the stent.

In FIG. 13b the stent 14 has the coating 76 of biocompatible material on the stent inner surface 80. The coating 76 forms a shell on the inner surface 80 of the stent 14, which can act to prevent the stent 14 from expanding, becoming dislodged, and/or contacting the contacting the patient's vasculature during stent delivery. The biocompatible material coating 76 on the inner surface 80 of the stent 14 may further improve stent retention during stent delivery where the bio-compatible material 76 has adhesive and/or non-slip properties that prevent the stent 14 from sliding along the balloon. The bio-compatible material coating 76 may serve to improve stent deployment by providing a smooth transition between the stent and a stent-deploying balloon as the balloon is expanded, which may involve unfolding of the balloon. The biocompatible material coating may help to smooth the inner surface of the stent after stent deployment, thereby providing a smoother lumen through which blood or other fluids can flow through the stent. As was the case with the outer coating of FIG. 13a, the inner coating of FIG. 13b may include portions of the coating 76 that extend into open areas of the stent 14, providing further opposition to expansion of the stent. The outer and inner coatings of FIGS. 13a and 13b, respectively, may be used in combination.

FIGS. 14 through 18 illustrate, by way of example, a method of delivering and implanting a stent 14 mounted on a balloon 24 of a catheter tube 22, including an embodiment of the biocompatible sheath 16. While the drawing figures illustrate a rapid exchange (Rx) intravascular catheter, embodiments of the retaining device may also be used with other delivery devices, including an over-the-wire (OTW) intravascular catheter. FIGS. 14–18 illustrate a situation in which the stent delivery system 10 having a biocompatible sheath 16 is used to deploy a stent 14 to support a dissected arterial lining to prevent the dissection 82 from collapsing into the arterial lumen 84 and impeding sufficient blood flow through the artery 86. Furthermore, the procedures and devices described herein may be adapted by one of ordinary skill in the art to any procedure where an endoprosthesis is to be placed into a body lumen.

Figure 16:
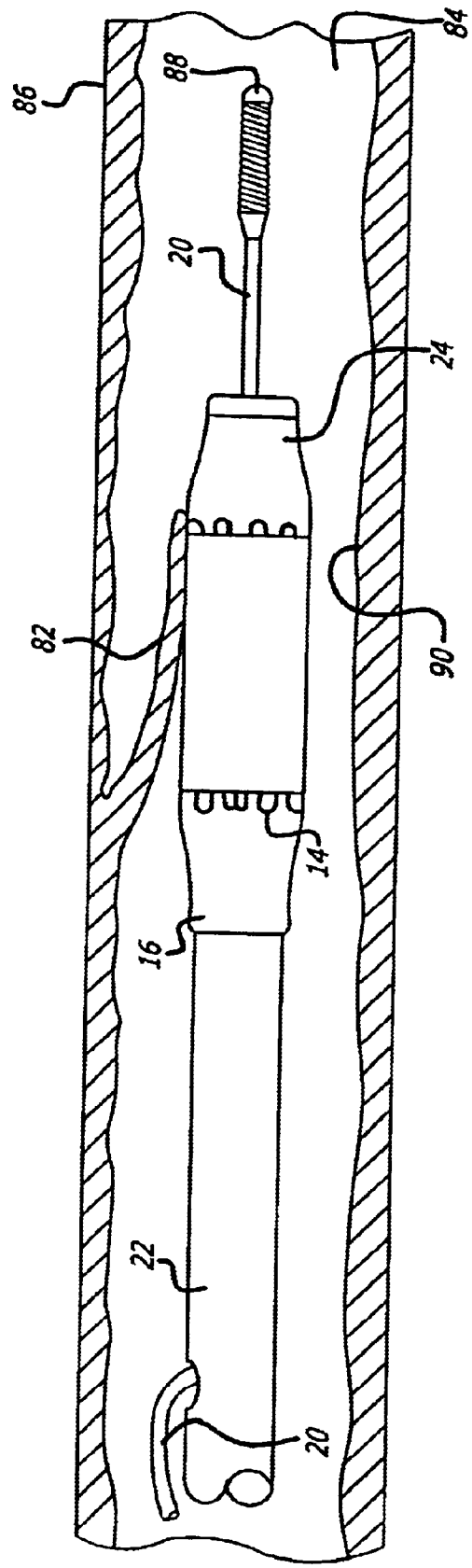
FIG. 16 depicts a partial side view of the stent delivery catheter assembly of FIG. 14, including a stent and bio-compatible material of the present invention, which has been positioned proximate to a dissected lining within a cross-section of a patient's vessel.

As shown in FIG. 14, a stent delivery assembly 10 is provided with biocompatible sheath 16 covering a stent 14 removably secured on an expandable member 24 formed on or secured to a catheter tube 22. Note that while a biocompatible sheath is depicted in FIGS. 14–18, other biocompatible configurations, such as the filaments, coatings, and inter-space materials of FIGS. 9–13, may also be used in a procedure such as the one depicted in FIGS. 14–18. Referring to FIG. 15, the stent delivery assembly 10 is inserted into the lumen 84 of an artery 86 along a guidewire 20 having a distal end 88, with the guidewire distal end 88 having been previously positioned past the dissection 82 requiring support. The expandable member 24, upon which the stent 14 and biocompatible sheath 16 are positioned, is then positioned proximate the dissection 82, as depicted in FIG. 16.

Figure 17:
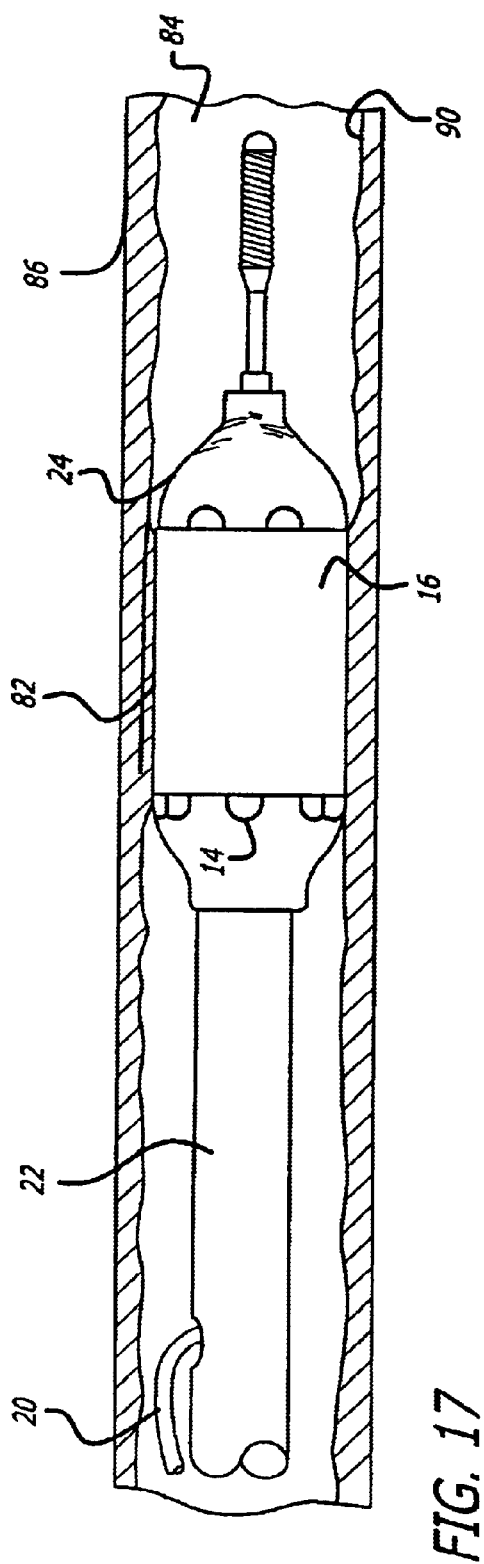
FIG. 17 depicts a partial side view of the stent delivery catheter assembly of FIG. 14, including a stent and bio-compatible material of the present invention, which has been positioned proximate a dissected lining within a cross-section of a patient's vessel, wherein the balloon and stent are fully expanded and the bio-compatible sheath has failed and/or relaxed.

As illustrated in FIG. 17, once the expandable member 24 and stent 14 are positioned at the dissection 82, the expandable member (balloon) 24 of the catheter tube 22 is inflated. This may be accomplished, for example, by injecting inflation fluid under substantial pressure into a lumen of the catheter tube. Once a first pressure is realized, which is less than the nominal inflation pressure of the balloon, the biocompatible sheath 40 fails. As the biocompatible sheath fails, the stent expands. As the balloon 24 continues to expand to its nominal (second) pressure, the stent 14 expands until it is fully expanded and implanted in the artery 86. The biocompatible sheath 16 is now positioned between the stent 14 and the arterial wall 90.

Figure 18:
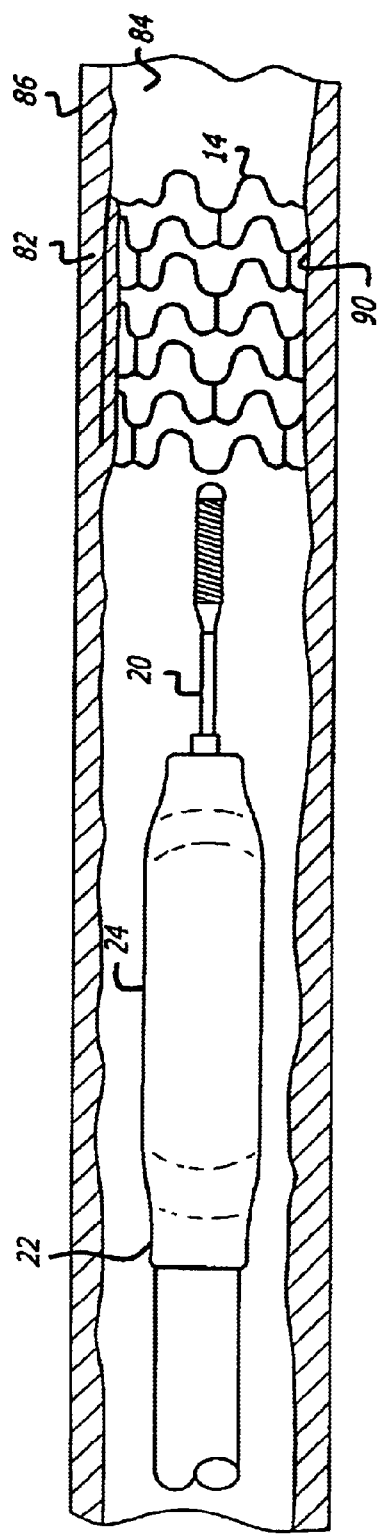
FIG. 18 depicts a partial side view of the stent delivery catheter assembly of FIG. 14, including a stent and biocompatible material of the present invention, wherein a stent and bio-compatible sheath have been deployed within a cross-section of a patient's vessel.

After the stent 14 is fully expanded, the expandable member 24 is contracted, such as may be achieved by deflating a catheter balloon. The delivery catheter 12 (including the catheter tube 22 and expandable member 24 balloon) and guidewire 24 are withdrawn from the vasculature, as depicted in FIG. 18, with the stent 14 and biocompatible material (in the form of the sheath 16) remaining behind.

As discussed above, the delivery catheter 12, as described herein, can have an over-the-wire (OTW) or rapid exchange (Rx) configuration as more fully disclosed in, but not limited to, U.S. Pat. No. 4,323,071 (Simpson et al.) (OTW); U.S. Pat. No. 4,573,470 (Samson et al.) (OTW); U.S. Pat. No. 5,501,227 (Yock) (Rx); U.S. Pat. No. 5,061,273 (Yock) (Rx); and U.S. Pat. No. 5,496,346 (Horzewski et al.) (Rx). Likewise, the stent 14, as described herein, can have various configurations, and suitable stents include, but are not limited to, the ACS MULTI-LINK STENT sold by Advanced Cardiovascular Systems, Inc., Santa Clara, Calif.; the NIR STENT sold by Boston Scientific, Natick, Mass.; and the MICRO STENT II and GFX sold by Arterial Vascular Engineering, Santa Rosa, Calif. Examples of suitable stents are disclosed in, but not limited to, U.S. Pat. No. 5,514,154 (Lau et al.).

The dimensions of the intravascular catheter will generally follow the dimensions of intravascular catheters used in angioplasty procedures in the same arterial location. Typically, the length of a catheter assembly for use in the coronary arteries is about one hundred thirty-five to one hundred fifty centimeters, the outer diameter of the catheter expandable member is about one millimeter, the length of the balloon is typically about two centimeters, and the inflated diameter of the balloon is about one to about five millimeters, depending upon the application. Catheter dimensions for peripheral use will vary, as is known in the art. The materials of construction of the catheter assembly, catheter tube, and expandable member maybe selected, for example, from those used in conventional balloon angioplasty catheters. Furthermore, the specific dimensions and materials of construction of the detachable sheath are provided as examples, and substitutes are readily contemplated which do not depart from the invention.

While the present invention has been described herein in terms of delivering an expandable stent to a desired location within a patient's blood vessel, the delivery catheter can also be employed to deliver stents and other endoprosthesis to locations within other body lumens. In addition, the biocompatible sheath may be used to cover and/or secure self-expanding and non-self-expanding stents on delivery catheters prior to deployment.

Although preferred and alternative embodiments of the invention have been described and illustrated, the invention is susceptible to modifications and adaptations within the ability of those skilled in the art and without the exercise of inventive faculty. Thus, it should be understood that various changes in form, detail, and usage of the present invention may be made without departing from the spirit and scope of the invention. Accordingly, it is not intended that the invention be limited, except as by the appended claims.

What is claimed is:

1. A catheter assembly for delivering an endoprosthesis within a body lumen, comprising:

a catheter;

an expandable member;

an endoprosthesis disposed on the expandable member, the endoprosthesis having a distal end and a proximal end; and a biocompatible material positioned on and heat bonded to the endoprosthesis, wherein the biocompatible material is configured to prevent expansion of the endoprosthesis;

wherein the biocompatible material comprises a sheath that surrounds a portion of the endoprosthesis, the sheath having a length less than the length of the endoprosthesis, and the sheath being positioned on the endoprosthesis so that the sheath does not overlie the distal end and the proximal end of the endoprosthesis.

2. The catheter assembly of claim 1, wherein the endoprosthesis is a self-expanding stent, and the biocompatible material provides inward pressure on the self-expanding stent to prevent expansion of the self-expanding stent.

3. An endoprosthesis for deployment in a body lumen, comprising:

a stent having a proximal end and a distal end; and a biocompatible material positioned on and heat bonded to the stent, wherein the biocompatible material is configured to prevent expansion of the stent;

wherein the biocompatible material comprises a sheath that surrounds a portion of the stent, the sheath having a length less than the length of the stent, and the sheath being positioned on the stent so that the sheath does not overlie the distal end and the proximal end of the stent.

4. The endoprosthesis of claim 3, wherein the stent is a self-expanding stent.

5. A method of delivering an endoprosthesis into a desired location within a body lumen, the method comprising:

providing a catheter assembly including a catheter, an expandable member, an endoprosthesis disposed on the expandable member, the endoprosthesis having a distal end and a proximal end, and a biocompatible material positioned on and heat bonded to the endoprosthesis, wherein the biocompatible material comprises a sheath that surrounds a portion of the endoprosthesis, the sheath having a length less than the length of the endoprosthesis, and the sheath being positioned on the endoprosthesis so that the sheath does not overlie the distal end and the proximal end of the endoprosthesis, and wherein the biocompatible material is configured to prevent expansion of the endoprosthesis but also to fail under sufficient pressure;

advancing the catheter, the expandable member, and the endoprosthesis through the body lumen;

positioning the expandable member and endoprosthesis at a desired location;

deploying the endoprosthesis and biocompatible material at the desired location, including the step of expanding the expandable member so as to cause the biocompatible material to fail and the endoprosthesis to expand;

contracting the expandable member;

withdrawing the catheter, the expandable member, and the sheath from the body lumen; and leaving the endoprosthesis and biocompatible material at the desired location within the body lumen.

* * * * *